(12) United States Patent
Michael et al.

(10) Patent No.: US 10,639,380 B2
(45) Date of Patent: May 5, 2020

(54) FLAVIVIRUS-BINDING, ENTRY-OBSTRUCTING, PROTEASE-RESISTANT PEPTIDE (RI57)

(71) Applicants: Scott F. Michael, Estero, FL (US); Sharon Isern, Estero, FL (US)

(72) Inventors: Scott F. Michael, Estero, FL (US); Sharon Isern, Estero, FL (US)

(73) Assignee: ENNAID THERAPEUTICS, LLC, Alpharetta, GA (US)

(*) Notice: Subject to any disclaimer, the term of this patent is extended or adjusted under 35 U.S.C. 154(b) by 171 days.

(21) Appl. No.: 15/369,893

(22) Filed: Dec. 6, 2016

(65) Prior Publication Data

US 2018/0155398 A1    Jun. 7, 2018

(51) Int. Cl.
*A61K 38/00*    (2006.01)
*A61K 47/64*    (2017.01)
*C07K 14/00*    (2006.01)

(52) U.S. Cl.
CPC .......... *A61K 47/643* (2017.08); *C07K 14/001* (2013.01); *A61K 38/00* (2013.01); *Y02A 50/385* (2018.01); *Y02A 50/391* (2018.01)

(58) Field of Classification Search
None
See application file for complete search history.

(56) References Cited

U.S. PATENT DOCUMENTS 7,491,794 B2 * 2/2009 Blatt .................... C07K 5/0804
                                                  530/317
8,541,377 B2 * 9/2013 Michael et al. ....... A61K 38/16
                                                  514/21.3

OTHER PUBLICATIONS

Guichard et al. (Proc. Nati. Acad. Sci., vol. 91, pp. 9765-9769) (Year: 1994).*

* cited by examiner

*Primary Examiner* — Sergio Coffa
(74) *Attorney, Agent, or Firm* — Richard L. Strauss, Esq.

(57) ABSTRACT

The invention pertains to inhibitors bindable to regions of a virus. More particularly, the invention relates to inhibitors bindable to regions of flaviviral envelope glycoprotein, or flaviviral virus E protein, a class II viral E protein. Even more particularly, the invention relates to peptides inhibitory to virus-to-cell fusion and virus entry into animal cells. The invention also contains methods of determining said inhibitors, bindable to regions of the flaviviral E protein complex, (e.g., those of dengue and zika viruses) as candidates for in vivo anti-viral compounds that are also resistant to degradation by peptidases and thus extraordinarily suitable for oral, in addition to other, routes of administration.

5 Claims, 12 Drawing Sheets

Specification includes a Sequence Listing.

DN57        N' - RWMVWRHWFHRLRLPYNPGKNKQNQQWP – C'

L-enantiopure (L-AA peptide)

RI57        N' - PWQQNQKNKGPNYPLRLRHFWHRWVMWR – C'

D-enantiopure (D-AA peptide & also retro-inverso of DN57)

Figure 3.

| Peptide | Virus | IC50 |
|---|---|---|
| DN57 | DENV-1 | 8.3 ±2.1 |
| | DENV-2 | 6.1 ±3.1 |
| | DENV-3 | 12.9 ±5.6 |
| | DENV-4 | 8.6 ±3.0 |
| RI57 | DENV-1 | 4.6 ±3.2 |
| | DENV-2 | 7.4 ±2.8 |
| | DENV-3 | 5.9 ±4.8 |
| | DENV-4 | 12.1 ±4.3 |

Figure 7.

FLAVIVIRUS-BINDING, ENTRY-OBSTRUCTING, PROTEASE-RESISTANT PEPTIDE (RI57)

GOVERNMENT SUPPORT

The U.S. Government owns a license in this invention and the right, in limited circumstances, to require the patent owner to license it to others as provided by the terms of the National Institutes of Health (NIH) grant no. GM068152.

TECHNICAL FIELD

The present invention relates to the field of therapeutic peptides. More specifically, this invention appertains to short-chain peptides capable of obstructing the bindable regions of flavivirus envelope glycoproteins, such as the E protein of dengue and Zika viruses, a class II viral E protein. Even more particularly, the invention relates to peptides inhibitory to virus-to-cell fusion and virus entry (the process that delivers the viral genome into the cell cytoplasm) into animal cells wherein the peptide inhibitors are resistant to degradation by peptidases. The subject invention also contains methods for determining said inhibitors, bindable to regions of the flavivirus E protein complex, for use as candidate in vivo anti-viral compounds that are also resistant to degradation by peptidases and thus extraordinarily suitable for oral, in addition to other, routes of administration.

BACKGROUND OF THE ART

A member of Flaviviridae, the flavivirus family, the dengue virus (DENV) arguably causes more pain, suffering, and economic hardship than any other mosquito-borne viral pathogen. Currently, there is no effective, specific treatment for infection, and methods proposed for controlling dengue virus by vector eradication (WHO, 2014) and vaccination (Dengue Vaccine Initiative, 2015) have been largely ineffectual, though such efforts continue. Other pathogenic arboviruses among the Flaviviridae cause Zika virus infection, yellow fever, West Nile virus disease, tick-borne encephalitis, Japanese encephalitis, and other insect-borne infectious diseases.

According to the World Health Organization (WHO), dengue fever incidences have increased dramatically in terms of number, severity of cases, and geographic scope over recent decades. Presently, WHO estimates that 40 percent of the world's population (~2.5 billion human beings) is at risk from dengue, that as many as 100 million new infections will occur each year and, that of these, 500,000 individuals should be hospitalized; unfortunately, most of those now afflicted have no access to adequate medical intervention. The dengue virus is carried by the mosquito, *Aedes aegypti* (and several less prominent species), and the range of this vector has been observed to have moved north and west in recent decades. In fact, in 2013, a number of cases were documented as having been contracted in Yunnan Provence, China and in Florida, US. Dengue infections present as flu-like illnesses that (increasingly, in recent years) progress to a more severe form known as Dengue Haemorrhagic Fever (aka, "severe dengue") that, in clinical settings, recently has been conflated with Ebola virus disease. Dengue is endemic in tropical and subtropical regions, worldwide, and is becoming increasingly problematic in urban and semi-urban areas of most Asian, Latin American, and Western Pacific countries. Severe dengue is a leading cause of hospitalization and death among children in affected regions. The virus occurs as four distinct, closely-related serotypes: DENV1, -2, -3, & -4. Again, like Ebola, although there is no specific treatment for dengue fever, early detection and proper medical attention can lower fatality rates to less than one percent. Unfortunately, although eventual resolution of episodic dengue infection seems to confer lifelong immunity against the offending clade, the patient remains largely susceptible to the other clades and, with successive infections, the chances of developing severe dengue increase significantly (WHO, 2014).

Like dengue, Zika is carried by mosquitoes of genus *Aedes* and, currently, there is no preventative or therapeutic directly active against the virus. Historically (since its original isolation in 1947), Zika infections occur asymptomatically in 80% of those affected and disease symptoms are common cold-like, and self limiting. Recently, Zika virus infections have been documented as showing significant increases in incidence, severity, and geographic scope. Owing to dramatic outbreaks in South America beginning in 2015; having moved beyond Tropical Africa and Southeast Asia; and its apparent capacity for teratogenicity causative of microcephaly and other CNS developmental problems; the fact that Zika may also be transmitted via sexual contact; and increased, associated occurrences of Guillain-Barre' syndrome, Zika has been classified as an "emerging disease" by The European Centre for Disease Prevention and Control (ECDC, 2016).

Enveloped viruses, once injected into a human host, are moved by thermodynamic diffusion until close enough to potential host cells for complementary membrane receptors to mediate adsorption and attachment of virions to cells. Flavivirus structural E protein receptors mediate both binding with and fusion to animal cells and are labeled as "class II" viral fusion proteins. The term "fusion machines" was coined to describe the dynamics of proficient cell ingress engineered by, so far as is now known, classes I through III viruses. Although the structural characteristics between the three classes are quite different, the mission supported is always the same—cell membrane recognition, attachment, and lipid bilayer fusion to accomplish cell entry by voracious, predatory viruses (Kielian, 2006; White, et al., 2008).

Among flaviviruses and alphaviruses, class II proteins are seen evolutionarily to have developed such that, although structurally diverse, they are mechanistically related in terms of their fusion-enabling architecture. As seen in class I proteins, a proteolytic cleavage occurs in class II virions yielding mature virions bearing primed fusion proteins. In the case of alphaviruses, pE2 proteins are cleaved to E2 and, for flaviviruses, the corresponding proteins are PrM and M. Again, as for class I viruses, the critical conformational changes activating fusion in class II are initiated by exposure to low pH that, in this case, reveals the fusion peptide formerly protected as a buried internal loop at the end of an elongated subdomain (Strauss & Strauss, 1994).

Although some of the pre-fusion structures of flaviviral and alphaviral envelope proteins have been determined, much work remains to be done in this area of research and the exact mechanism underlying the modus operandi of class II viral fusion proteins remains to be elucidated. For this reason, at least in part, no therapeutic specifically able to inhibit the fusion of such proteins and consequent infectivity of this virus class has been developed (van der Schaar, et al., 2007). An urgent, unmet need currently exists for the discovery and practical development of cell-entry inhibitors specifically designed to inhibit infection by flaviviruses, alphaviruses, and hepatitis viruses. Given, membrane fusion is a vital step in the progression of class II viral pathogenesis, a more complete description of the structure and function of envelope proteins is required for purposes of producing effective therapeutic and preventative agents against flavi-, alpha-, and hepatitis viruses.

U.S. Pat. No. 8,541,377 (the '377 patent) discloses peptides that are virus-to-cell fusion- and entry-inhibitors bindable to regions in class II E viral proteins. That patent discloses compounds and methods for screening compounds potentially active against these bindable regions to discover therapeutic candidates for fighting disease viruses bearing class II E proteins; these include dengue fever, dengue hemorrhagic fever, tick-borne encephalitis, West Nile virus disease, yellow fever and, possibly, hepatitis C. Further, it discloses a method for identifying E protein topographical regions bindable by an artificially-synthesizable and highly specific peptide. Said peptide can be configured demonstrably to act with sufficient degrees of affinity and avidity; further, such virus binding can be assayed either in vitro and, likely, in vivo. Further, it also may be utilized in structure determination, drug screening, drug design, and other methods described and claimed in the '377 patent. Methods for inhibiting viral infection, measuring same, and (theoretically) treating dengue-induced diseases are provided using methods that employ peptides and derivatives thereof to inhibit dengue virus-to-cell binding using a cell entry-inhibitory peptide comprised of 28 amino acids (AAs) arranged in the following sequence: (seq. intentionally redacted), identified as DN81 and labeled SEQ ID NO: 1 for purposes of and within, that particular patent.

No particular isomeric form of DN81 is disclosed within the '377 patent. This, ordinarily, is not surprising because when a given peptide sequence is found to have a desired property—for example, binding to a particular receptor site—it is expected that one isomeric form, and only one isomeric form of the peptide—within a racemic mixture—will have an effective binding conformation. The other isomeric form, e.g., the L- or D-enantiomer, will have no, or very little, binding capability. The obvious reason for effective binding being provided by only one isomeric form is that such binding is highly related to, and controlled by, the 3-dimensional conformation of the peptide and its ability to position a residue sequence aligning with a residue sequence forming a binding site(s) within or upon a target virion. Thus, binding found between such peptides and a target AA sequence found, for example, within the flavivirus II E envelope protein, is controlled by the 3-dimensional conformation of both binding site and a putative therapeutic peptide under physiological conditions. Thus, considering L- and D-forms of such binding peptides display "mirror image" conformations, it is expected and ordinarily found that only one isomer (virtually always, L-) is biologically active and can participate in effective binding.

Despite the fact that the binding qualities of a therapeutic peptide are provided by only one enantiomeric form, knowing which particular isomeric form is effective is unnecessary as, ordinarily, there will be a sufficient concentration of the effective isomer within the racemic mixture to provide the desired effect.

Although not discussed in the '377 patent, DN81 (as were many different candidate peptides) was designed and synthesized exclusively as the enantiopure, L-form peptide for testing—as the "L-" enantiomer is almost always, as discussed above, the form effective in providing binding. Although oral dosing with DN81 was originally contemplated, among various, potentially less efficacious forms of administration for therapeutic purposes, it is now understood that digestion by peptidases effectively precludes this possibility. This is, of course, unfortunate as providing a therapeutic capable of oral administration would be expected to increase greatly the number of individuals who could and would accept treatment and, thereby, effectively reduce the number of individuals infected with, and harboring (and potentially disseminating), such viral pathogens.

Many areas of the world heavily affected by flaviviral infections also contain populations with severely limited access to modern medical technologies. Effectively treating, curing, and preventing such infections must be accomplished by means of a methodology that not only blocks viral entry, but also enables and encourages compliance through efficient administration of the therapeutic agent. Oral, as opposed to parenteral, administration would be highly favored for such purposes and, particularly so, for treating pediatric patients. Oral administration in medically-underserved regions, also should obviate the use of injections and the clear possibility of passing blood-borne infections such as HIV and viral hepatitides when needles and syringes are reused. Clearly, there is an absolute, heretofore, unmet need for the development of effective anti-flaviviral therapeutics that can be administered orally.

To develop a therapeutic peptide capable of binding with ligands within flaviviral class II E envelope proteins to interfere with virus-to-target cell binding and fusion would be highly desirable—and even more so—if such peptide were resistant to the degradative actions of peptidases. The development of a peptidase-resistant peptide would likely enable oral (and several other routes of administration that risk exposure to peptidases) delivery of said therapeutic to animals subject to flaviviral infections.

SUMMARY OF THE INVENTION

Now, in accordance with the present invention, a novel method is disclosed for screening peptide compounds for the purpose of identifying a specific and identified stereoisomeric conformation. The specific stereoisomeric conformation to be screened for and identified provides and includes a sequence of residues—under ordinary physiologic (chemical, temperature, and pH) conditions in which a target host cell is ordinarily found—capable of aligning and binding with specific ligands present and located upon regions of a flavivirus virion's class II E protein. The specific ligands present upon the class II E protein refer to those amino acid sequences which ordinarily enable the interaction of said envelope protein with complementary residue sequences presented by target host cells to enable binding, fusion, and infection of the host target cell. Thus, the identified peptides are useful for blocking such virions from binding, fusing with, and infecting target host cells. Of great importance, the disclosed method identifies enantiopure isomers comprising peptides highly resistant to degradation by various naturally-occurring proteases so as to enable oral administration.

The method of the present invention screens for enantiopure peptide sequences useful in the treatment of flaviviral infections inclusive of: dengue fever, dengue hemorrhagic fever, Zika virus infection, tick-borne encephalitis, West Nile virus disease, yellow fever, and hepatitis C. The present invention also discloses specific therapeutic residues providing the aforementioned binding properties—effectively, to reduce and/or eliminate flavivirus binding and infectivity while also enabling oral administration of such therapeutics. Further, the present invention also discloses means of increasing the effectiveness of the aforementioned therapeutic peptides by replacing and/or adding specific identified residues and/or compounds thereto.

The present invention also discloses a protease-resistant flavivirus-targeted cell entry-inhibitory peptide comprising an enantiopure d-amino acid having an amino acid sequence identified herein as SEQ ID NO: 1.

A further preferred embodiment of the present invention provides a method for preventing (dengue fever, Zika virus, and other) flaviviral infections that includes inhibiting binding and fusion between the virion envelope protein and an animal host target cell membrane, the process that delivers the viral genome into the cell cytoplasm. The aforementioned embodiment of the present invention may also be utilized, as discussed below, to treat individuals already infected with dengue fever, Zika virus, and/or other flaviviral infections.

DETAILED DESCRIPTION OF THE INVENTION

Any peptide or protein that inhibits the fusion between the flavivirus (dengue, Zika, etc.) virion envelope protein and a target host cell membrane, including both human as well as nonhuman hosts, and is resistant to proteases may be used according to the method of the present invention to prevent and/or treat infection by flaviviruses. In various embodiments of the invention, these peptides inhibitory to flavivirus entry into animal cells may include, but are not limited to, peptides related to several membrane-interactive bindable regions of flaviviral proteins.

Comprised of a single strand of positive-sense RNA, the flavivirus genome encodes three structural (C, capsid; M, membrane; & E, envelope) and seven nonstructural (NS1; NS2 [A&B]; NS3; NS4 [A&B]; and NS5) proteins. The genomic organization of the dengue virus highlighting the E protein gene is illustrated in FIG. 1, below. The NS genes code replication and assembly products completing the processes using host cell resources. The complete virus is ~50 nm in diameter, spherical, and carries the genome within a nucleocapsid enveloped by a lipid bilayer (viral envelope). The viral envelope is embedded with M & E proteins that control attachment and entry into host cells. In the host cell, the M protein is synthesized as a precursor protein (prM) thought to act as chaperon in the folding and assembly of E glycoproteins on the mature virion surface. This process, evidently, is responsible for infectious incursion into host cells by enabling binding sequences of amino acids thereupon to align, via conformational adjustment, with binding receptor sites formed by complementary amino acid sequences presented by the target cell membrane (Guzman, et al., 2010).

Throughout this specification and claims, the term "bindable viral region", when used in reference to a peptide, amino acid sequence, nucleic acid complex and the like, refers to a section of a flavivirus E protein or other class II E protein that provides a target or a likely target—or ligand—for binding; for example, a peptide agent that reduces or inhibits viral infectivity. For a peptide, a bindable peptide region generally refers to a segment wherein several AAs of that peptide would be capable of interacting with at least a portion of the bindable viral region of the flaviviral E protein—which may comprise a ligand. For a peptide or complex thereof, bindable regions include binding pockets and sites, interfaces between domains of a peptide or complex, surface grooves, contours, or surfaces of a peptide or complex capable of participating in interactions with another molecule, such as may be located in the surface of a cell membrane.

In a preferred embodiment of the present invention, a peptide that inhibits flaviviral fusion onto, and entry into a host target cell, and also demonstrates high levels of protease resistance, is the enantiopure D-peptide "RI57" presenting the residue sequence: (SEQ ID NO: 1). RI57 was synthesized as a novel, enantiopure, retro-inverso-variant stereoisomer of another peptide, DN81. DN81 has also been referred to as DN57 or DN57opt, in at least one publication: (see Costin, et al., 2010 and, citing, Xu, et al., 2012). DN81 was disclosed and was the central subject of the '377 patent. However, unlike DN81, RI57 is comprised of only D-AAs (non-chiral AA, glycine, excepted)—a reverse isomeric configuration that, surprisingly and unexpectedly, has shown great efficacy. To illustrate the difference between "L-" and "D-" isometric conformations, the reverse conformation of DN81 as compared to R157 (SEQ ID NO: 1), FIG. 2 schematically demonstrates the anatomy of a retro-inverso peptide with FIG. 2A depicting a tripeptide comprised of three L-AAs bearing side groups highlighted in blue, red, and green for clearer tracking. FIG. 2B shows a different tripeptide made as the D-form of the same three AAs with the same side groups colored, but with the sequence inverted.

The D-enantiomer of DN81 neither has been synthesized nor tested, heretofore. As discussed above, since it was highly unlikely ever to find a "D-" enantiomer providing the binding properties of an "L-" isomeric peptide, there was no reason to assemble such. As the D-retro-inverso-peptide of DN81, RI57 possesses a similar arrangement of side-chains, but with carboxyl and amino groups oppositely oriented. FIG. 3, presents the full single-letter-code AA sequences of the L-AA-containing DN57 and the D-AA-containing RI57 for comparison.

The development of peptide-based immune-, neuronal-, hormonal-, anti-neoplastic, antibiotic-, etc., mediators has long been hampered by peptide lability to proteolysis upon both oral and—to a lesser, but significant extent—parenteral administrations. Some peptide chemists are beginning to consider that, for small peptides able to bind independently of a secondary structure, an L-peptide and its D-retro-inverso-peptide might show similar binding affinities with a particular target L-protein. However, as it turns out, even after two decades' intensive work on topic, the possibilities for success of synthesized peptide analogues with both retained (and possibly enhanced) biological activities and also half-lives (particularly with respect to proteolysis resistance) remain largely speculative with any positive outcome rare and unpredictable. Theoretically, there is reason to believe such peptidomimetics containing D-AA residues or reversed peptide bonds, advantageously, may be non-immunogenic (Guichard, G., et al., 1994); although this prospect has not yet been tested for subject peptides, protein BLAST searches for homology with RI57 have been, expectedly, fruitless. It is also known that retro-inverso isomers only rarely have been seen to retain the binding activities of their parent L-peptides (Li et al., 2010). In the course of their statistical analysis of proteome-wide post-translational modifications (PTM) using the Swiss-Prot database, a Princeton University group found that, of an approximately $1.9\times10^8$ AA dataset, only 837 D-isomers were observed—a variant frequency of ~$4.4\times10^{-6}$! Of these rarely occurring PTM, D-alanine accounted for 79.3 percent, representing incidences six times that of D-serine, the next most abundant D-AA observed in proteins affected by PTM (Khoury, et al., 2011).

Due to the rather poor performance of D-AA peptides in providing any of the activity of their "L-" enantiomer counterparts, RI57 was conceived, synthesized, and tested on no more than a whim. Quite surprisingly and serendipitously, as discussed below, it has proven to be highly capable of blocking cell entry by DENV and Zika virus (despite its D-AA content) and, remarkably, at the same time, has demonstrated a pronounced resistance to peptidase degradation not provided by its "L-" counterpart (also discussed, below).

In a further embodiment of the present invention, homologous peptides are included as related to the flavivirus entry-inhibitory peptide. The term "homologous flavivirus entry-inhibitory peptide" as used throughout this specification and claims, refers to peptides bearing a sequence identical to the corresponding portion of the flaviviral inhibitory protein and peptides in which one or more AAs are substituted by functionally equivalent AAs. For example, homologous flaviviral entry-inhibitory peptides include, but are not limited to, benzylated and glycosylated derivatives thereof (and, conceivably, peptides including enantiomers of naturally-occurring AAs).

In additional embodiments of the invention, the dengue fusion- and entry-inhibitor peptide, related peptides, or derivatives thereof may be linked to carrier molecules including proteins. Proteins contemplated as possibly useful include, but are not limited to, human serum albumin (HSA). According to the invention, flaviviral fusion- and entry-inhibitor peptides comprising up to 20 percent additional, or fewer, AAs are also contemplated as useful.

The candidate therapeutic flavivirus-inhibitory, protease-resistant peptides of this invention are expected to be useful in blocking virion-to-cell fusion and entry and, thereby, treating flavivirus infections in any animal species susceptible to such infection and developing consequent illnesses. Animals at risk and potentially "patients" may include, but are not limited to, humans, dogs, cats, horses, birds, etc . . . . The peptides of the invention may be administered to infected individuals in any sterile, biocompatible pharmaceutical carrier, including—but not limited to—saline, buffered saline, dextrose, aerosolized surfactant/spreading agent, and water. Routes of administration of these peptides in veterinary or human patients are well-known to those skilled in the art and may include—but are not limited to—oral, intranasal, inhalation, intramuscular, intravenous, subcutaneous, intradermal, intraperitoneal, rectal suppository, and trans-blood-brain barrier delivery (to the central nervous system). However, the present invention provides flaviviral fusion- and entry-inhibitor peptides permissive of oral administration due to their inherent resistance to degradation by digestive enzymes.

As and when appropriate, subject putative therapeutic peptide will be tested to determine therapeutic indices (TI), first in animal models and then in human beings (eventually, on an individual basis). The ultimate goal of experimentation through the clinical level will be to determine an optimal TI for subject flavivirus-binding, entry-obstructing, protease-resistant peptide candidate therapeutic peptide. Pharmacodynamic assessments of clinical safety and efficacy, relative to observations tracking responses to increasing doses, ranging from no effect, toxicity ($TD_{50}$), through lethal effect will be carried out and analyzed to identify a therapeutically effective dose (EDO for human populations residing in the ratio TD50/ED50=TI. Naturally, said experimentation will take into account many clinically relevant factors including administration methodologies/routes while measuring and correlating pharmacokinetic variables including drug plasma levels, rates of decay, metabolites (if any), host immune responses, vital signs and, of course, viral load and other possible measures of infection with host symptomatology.

Various methodologies are available for screening, detecting and enumerating, selecting, and designing biological molecules that can usefully interact with the dengue and Zika virus E, other class II E proteins, or other structurally similar molecules. Based on information derived using such techniques, it is possible to isolate or design molecules endowed with specific structural/conformational qualities complementary to "druggable" regions on the dengue virus, Zika virus, other viruses carrying class II E proteins, or equivalent entities. The term "druggable" as utilized within this specification and in the claims refers to regions and proteins along the flaviviral envelope that present a sequence of amino acids which, when bound by a complimentary sequence of a fusion- and entry-inhibitor peptide, are rendered unavailable for binding the flaviviral virion to a target host cell. For such purposes, drug design procedures may benefit from computational modeling and analysis software programmed to assist in estimating the potential sufficiency of any theorized candidate peptide in terms of affinity and avidity for class II viral E protein receptors comprising bindable/druggable regions on DENY, Zika virus, and related viruses (e.g., Xu, et al., 2012). Very generally, flaviviral fusion- and entry-inhibitor peptides targeting E proteins may be designed using data from sequenced primary AAs applied to Monte Carlo binding algorithms (Falcioni & Deem, 1999) that generate random values for allowed variables, in association with Wimley-White interfacial hydrophobicity scales. The Wimley-White scale simulates membrane protein topography and related surface characteristics using hydropathy plots with respect to thermodynamic principles. An excellent review of such computational design approaches is provided by Liang, J., et al., 2012.

BRIEF DESCRIPTION OF THE DRAWINGS

FIG. 3 illustrates both DN57 and RI57 AA sequences.

FIG. 7 charts half-maximal inhibitory concentrations of DN57 and RI57 v. DENY (see table 4.).

DESCRIPTION OF EXPERIMENTAL TECHNIQUES AND EVIDENCE THEREFROM

Figure 1:
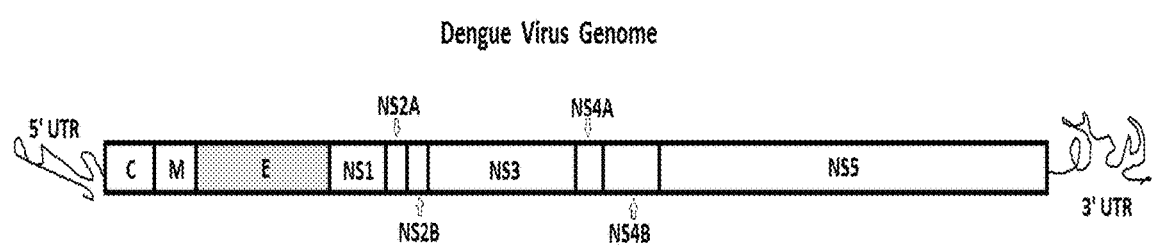
FIG. 1 illustrates the genome and morphology of a representative flavivirus (the dengue virus).
Figure 2:
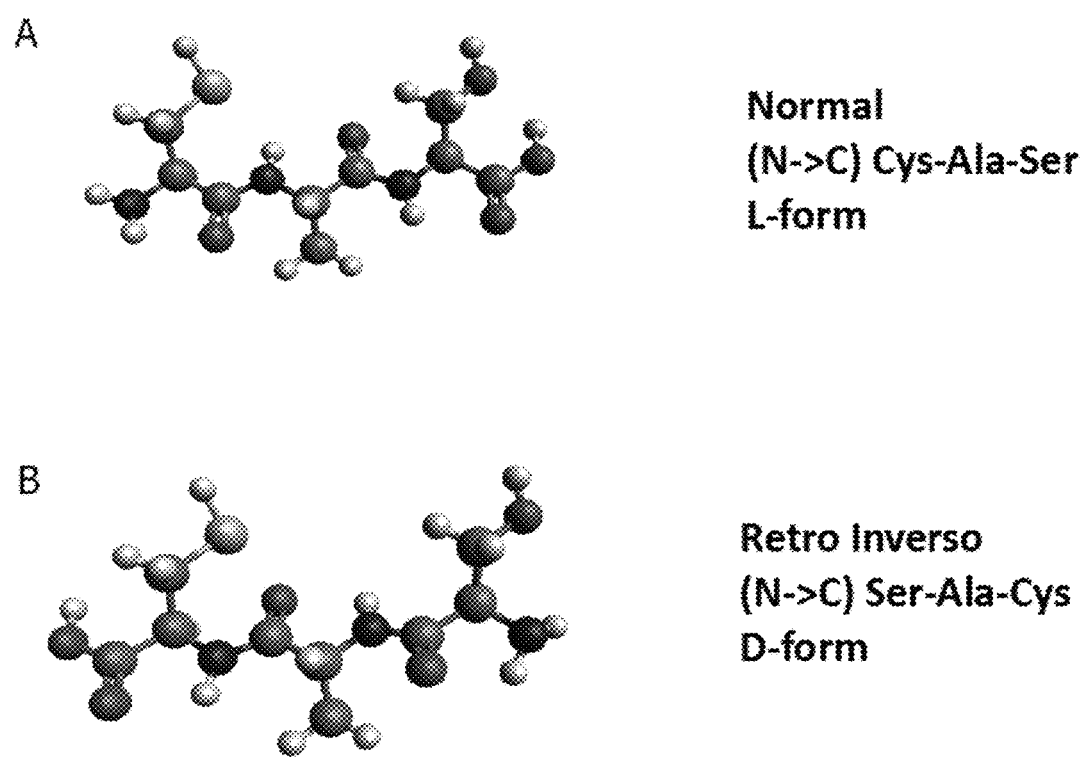
FIG. 2 illustrates the conformation of a retro-inverso peptide.

Preparation of Dengue Fusion- and Entry-inhibitor Peptides

Candidate therapeutic peptides may be isolated from naturally-occurring or recombinant viral proteins. Alternatively, they may be synthesized by means of standard recombinant DNA methodologies. In this case, a desirable peptide is produced by a microorganism carrying recombinant nucleic acid molecules able to encode the peptide of interest under the control of a suitable transcriptional promoter and it then is isolated and harvested. Any suitable methodology known in the art including, but not limited to, Merrifield solid phase synthesis (Clark-Lewis et al., 1986) may be used to produce the peptides of the invention. For present purposes, all experimental peptides were synthesized as enantiopure using solid-phase conventional N-a-9-fluorenylmethyloxycarbonyl chemistry (Genemed Synthesis, San Francisco, Calif.), purified by reverse-phase HPLC chromatography, and assayed with AA analysis/electrospray mass spectrometry. Stock solutions of peptides were suspended in v/v 20% dimethyl sulfoxide and v/v 80% HOH and concentrations determined by aromatic side chain absorption spectrometry set at 280 nm. As needed, scrambled peptide sequences were ordered by random choices from a pool of the same AA composition as the candidate therapeutic peptides tested.

Viruses and Cells

The WHO, Arbovirus Reference Laboratory, University of Texas, Medical Branch (UTMB) Galveston provided four dengue virus clades for purposes of experimentation; namely: DENV1 (strain HI-1), DENV2 (strain NG-2), DENV3 (strain H-78), and DENV4 (strain H-42). The original Ugandan (766) strain of Zika virus was also obtained from the Arbovirus Reference Laboratory. Viruses were propagated in the African green monkey kidney epithelial cell line, LLC-MK2, from the Arthropod-borne and Infectious Diseases Laboratory, Colorado State University. LLC-MK2 cells were maintained in Dulbecco's modified eagle media (DMEM) with v/v 10% fetal bovine serum (FBS); 2.0 mM Glutamax, 100 U/ml penicillin G, 100 µg/ml streptomycin, and 0.25 µg/ml amphotericin B; and incubated at 37° C. with v/v 5% $CO_2$ in air.

Statistical Analyses

Throughout the course of the experimentation described, Graphpad Prism 4.0 software (San Diego, Calif.) was used to perform the statistical analyses with p values of less than 0.05 considered significant and the graphic representations of these data were generated by means of Origin 6.0 graphing software (Northampton, Mass.).

Cytoxicity Assay of Therapeutic/Inhibitory Peptides

Possible direct cytotoxicity caused by peptide exposure to proliferating LLC-MK2 monolayers was measured using the TACS™ MTT cell proliferation assay (R&D Systems, Inc., Minneapolis, Minn.) according to the manufacturer's instructions. The MTT assay detects and measures mitochondrial reductase activity observable in viable cells. Peptides at various dilutions in serum-free DMEM were added to confluent monolayers of LLC-MK2 cells in 96-well plates for 1 h at 37° C., similar to the focus-forming inhibition assays, and subsequently incubated at 37° C. with 5% $CO^2$ for 24 h. A Tecan GeniosPro plate reader (Tecan US, Durham, N.C.) was used to measure absorbance at 560 nm.

To determine whether observed DENV-inhibition effects were due to cellular toxicity—as a result of exposure of host cells to the inhibitory peptides—impacting viral replication, the effect of the peptide on mitochondrial reductase activity of the target cells was measured over the concentration ranges that caused viral inhibition. No sign of toxicity was observed with any compound as compared with medium-only controls (p>0.05, ANOVA with Dunnett's post hoc test) when tested on confluent cell monolayers arranged to replicate conditions of focus-forming assays.

TABLE 1

Low Levels of Toxicity in Host LLC-MK2 Cells from DN57 and RI57 Peptide Exposures.

| A | | | B | | |
|---|---|---|---|---|---|
| [DN57] uM | % Viable | ±sd | [RI57] uM | % Viable | ±sd |
| 0.0 | 100.0 | 3.6 | 0.0 | 100.0 | 4.6 |
| 0.1 | 100.1 | 8.8 | 0.1 | 95.9 | 1.3 |
| 0.5 | 98.6 | 5.7 | 0.5 | 96.5 | 3.4 |
| 1.0 | 100.2 | 8.9 | 1.0 | 95.0 | 3.1 |
| 5.0 | 97.8 | 5.0 | 5.0 | 95.9 | 6.1 |
| 10.0 | 95.9 | 4.6 | 10.0 | 95.3 | 8.1 |
| 15.0 | 92.8 | 5.8 | 15.0 | 100.3 | 2.8 |
| 20.0 | 76.4 | 16.1 * | 20.0 | 100.8 | 4.9 |
| 25.0 | 80.2 | 14.3 * | 25.0 | 101.3 | 3.4 |
| 30.0 | 54.7 | 11.9 * | 30.0 | 104.2 | 3.5 |
| 35.0 | 55.1 | 2.6 * | 35.0 | 94.3 | 2.7 |
| 40.0 | 50.6 | 1.1 * | 40.0 | 92.0 | 5.5 * |

Figure 4:
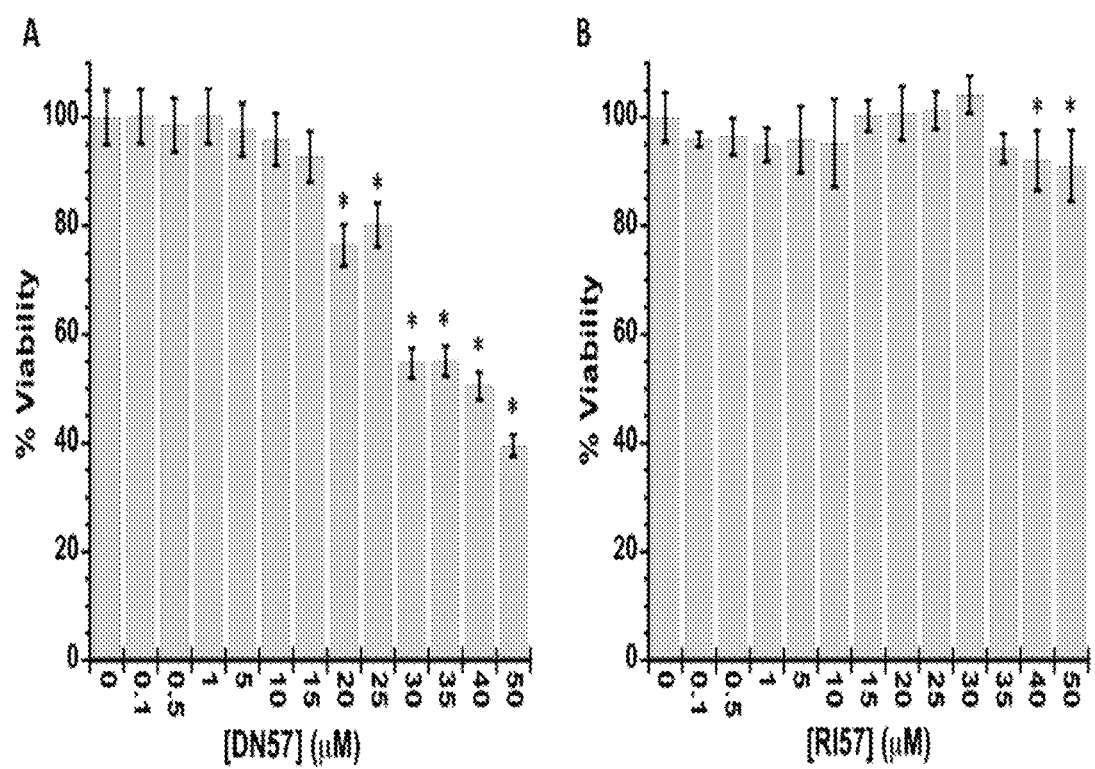
FIG. 4 charts the relative toxicity to host cells of DN57 and RI57 (see table 1.).

Table 1. depicts the results of viability tests showing that the inhibitory activity of the RI57 peptide is not due to cellular toxicity (as plotted and shown in FIG. 4). Mitochondrial reductase activity (MTT) following incubation with increasing concentrations of (A) DN57 or (B) RI57 peptide as a measure of LLC-MK2 target cell viability is plotted. Error bars show ±standard deviations (±sd) of the means with an asterisk indicating instances of statistically-significant differences from control according to Dunnett's post hoc test (p<0.05).

Focus-Forming Unit (FFU) Assay

The FFU assay was performed essentially as previously described by Hrobowski, et al., 2005. Twenty-four hours prior to infection, LLC-MK2 target cells were seeded at a density of $1.0 \times 10^5$ cells per well of an E-well plate. Approximately 200 FFU of virus were incubated with or without peptides in serum-free DMEM for 1 h at 20° C. Virus/peptide or virus/control mixtures were allowed to infect confluent target cell monolayers for 1 h at 37° C., rocking every 15 min, after which time the medium was aspirated and monolayers overlaid with fresh DMEM plus v/v 10% FBS containing v/v 0.85% Sea-Plaque Agarose (Cambrex Bio Science, Rockland, Me.). To allow proper setting, monolayers with agar overlays were incubated 20 min at 4° C. Next, infected cells were incubated at 37° C. with 5% $CO_2$ for three days (DENV1, -3, and -4) or five days (DENV2). Then, infected cultures were fixed with 10% formalin overnight at 4° C., permeabilized with v/v 70% ethanol for 20 min, and rinsed with phosphate-buffered saline, pH 7.4 (PBS) prior to immunostaining. Viral foci were detected and enumerated using supernatant from mouse anti-DENV hybridoma E60 (obtained from the Department of Pathology & Immunology, Washington University, St. Louis, Mo.) followed by horseradish peroxidase-conjugated goat anti-mouse immunoglobulin (Pierce, Rockford, Ill.) and developed using AEC chromogen substrate (Dako, Carpinteria, Calif.). Results have been expressed as an average of two independent trials (at least) with three replicates each.

Peptide Candidate Assessments for Ability to Inhibit Denv1-4 Infectivity

Figure 5:
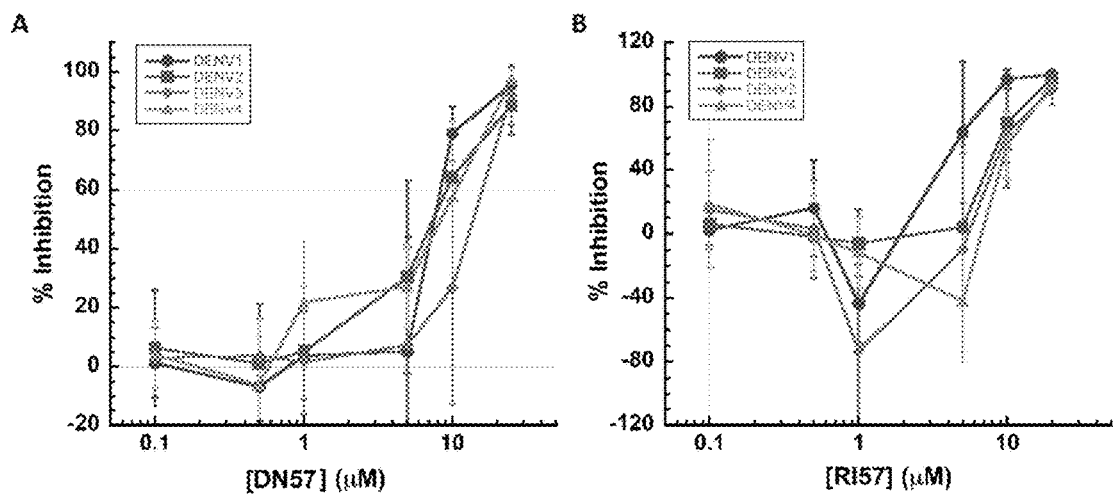
FIG. 5 graphs in vitro inhibition of dengue virus by DN57 and RI57 (see table 2A, 2B.).

Inhibitory activities of each peptide against DENV1-4 were quantitated by means of focus-forming assays performed as described and dose-response curves generated over concentration ranges dictated by the solubilities of the peptides in a 1% DMSO/aqueous solution; these results are presented below in Table 2. and as plotted in FIG. 5.

TABLE 2

(A&B). In Vitro Inhibition of Dengue Virus (Clades 1-4) Infection.

| | % Inhibition | | | | | | | |
|---|---|---|---|---|---|---|---|---|
| | DENV1 | ±sd | DENV2 | ±sd | DENV3 | ±sd | DENV4 | ±sd |
| A [DN57] uM | | | | | | | | |
| 0.1 | 1.3 | 11.7 | 6.3 | 19.7 | 3.0 | 12.5 | 4.3 | 11.4 |
| 0.5 | −6.8 | 23.1 | 1.2 | 19.9 | 3.7 | 6.8 | −6.2 | 22.8 |
| 1.0 | 3.8 | 15.0 | 5.1 | 21.6 | 1.7 | 25.2 | 21.8 | 20.6 |
| 5.0 | 5.3 | 38.7 | 30.4 | 32.7 | 7.3 | 33.2 | 27.2 | 13.9 |
| 10.0 | 79.1 | 9.3 | 64.2 | 20.1 | 26.6 | 39.4 | 57.4 | 25.7 |
| 25.0 | 95.8 | 6.5 | 88.7 | 10.3 | 92.2 | 10.4 | 97.2 | 3.8 |
| B [RI57] uM | | | | | | | | |
| 0.1 | 2.4 | 11.9 | 6.2 | 13.0 | 15.1 | 24.6 | 18.9 | 39.8 |
| 0.5 | 16.2 | 29.9 | −1.7 | 20.9 | 3.3 | 30.9 | −0.7 | 25.0 |
| 1.0 | −43.6 | 24.4 | −5.9 | 21.0 | −73.1 | 65.7 | −11.8 | 21.7 |
| 5.0 | 63.8 | 44.8 | 4.3 | 46.0 | −9.7 | 64.0 | −41.8 | 38.2 |
| 10.0 | 97.3 | 5.8 | 69.8 | 25.4 | 63.3 | 34.6 | 55.5 | 21.0 |
| 20.0 | 100.0 | 0.0 | 97.8 | 1.4 | 90.1 | 8.5 | 94.4 | 6.2 |

Whereas, the control 1% DMSO/PBS solutions showed no DENV inhibitory activity in this assay system (data not shown), both DN57 and RI57 peptides showed inhibitory activity that increased with their concentrations. Scrambled sequences of the DN57 and RI57 peptides also showed no sign of DENV2 infectivity inhibition (data not shown). Overall, the inhibitory effects of both peptides approached 100% at their optimal concentrations.

Inhibitory activity of RI57 against Zika virus was quantitated by means of focus-forming assays performed as described and dose-response curves generated over concentration ranges dictated by RI57 solubility in a 1% DMSO/aqueous solution; these results are presented below in Table 3. and as plotted in FIG. 6.

TABLE 3

In Vitro Inhibition of Zika Virus Infection.

| [RI57] uM | % Inhibition | ±sd |
|---|---|---|
| 0.0 | 0.0 | 13.2 |
| 0.1 | 8.7 | 12.8 |
| 0.5 | −10.0 | 30.1 |
| 1.0 | −21.3 | 39.1 |
| 5.0 | −43.8 | 13.1 |
| 10.0 | 4.9 | 22.6 |
| 20.0 | 71.0 | 22.5 |
| 35.0 | 95.8 | 2.8 |

Whereas, the control 1% DMSO/PBS solutions showed no Zika inhibitory activity in this assay system (data not shown), RI57 showed inhibitory activity that increased with concentration. As for DENY, RI57 inhibited Zika virus infection at levels approaching 100%. RI57 is thus shown to be effective in the inhibition, binding, fusion, and infection caused by the Zika.

$IC_{50}$ Results for DN57 and RI57

Figure 6:
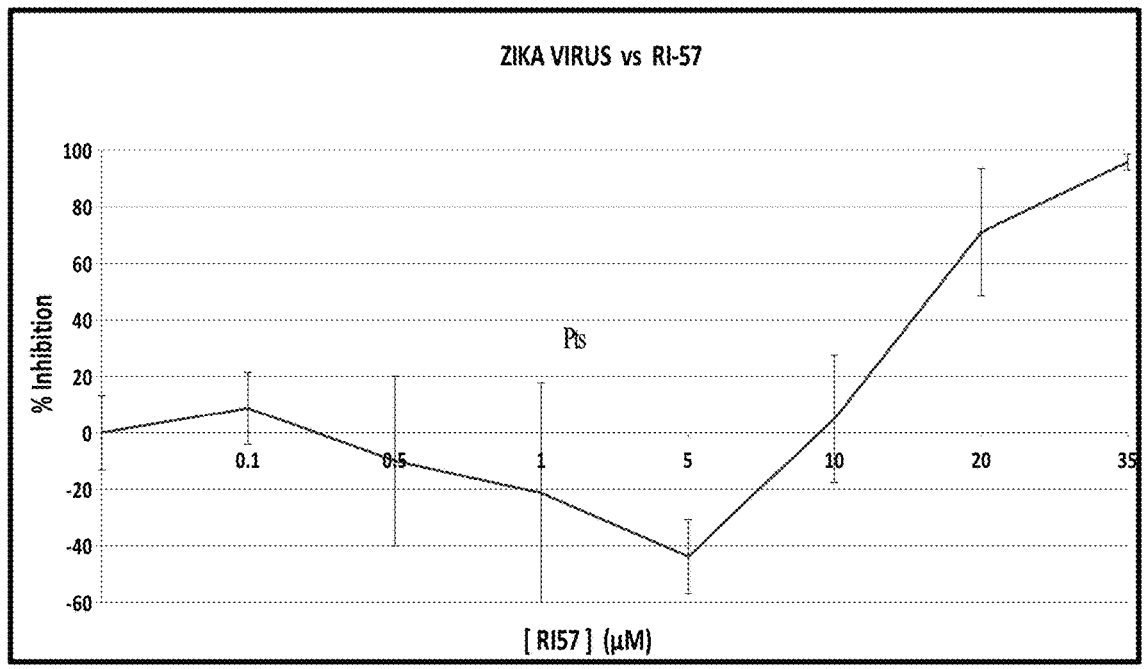
FIG. 6 graphs in vitro inhibition of Zika virus by RI57 (see table 3.)
Figure 8:
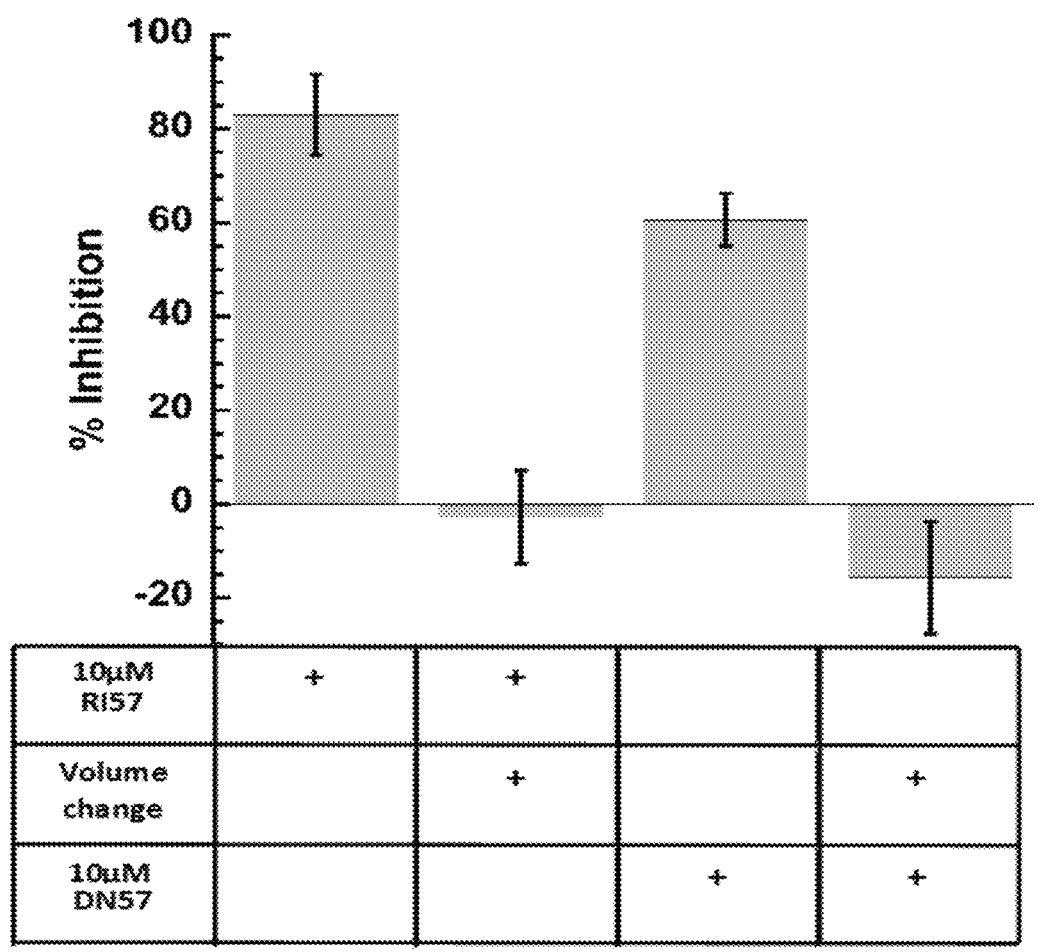
FIG. 8 charts reversible binding of both DN57 and RI57 (see table 5.).

Table 4. depicts half-maximal inhibitory concentrations ([μM]) comparatively estimated for the effect of DN57 and RI57 on each of the four DENV clades by sigmoidal curve-fitting to each dose-response curve in FIG. 6. Errors are reported as ±sd of the means and these results also are shown in FIG. 7.

TABLE 4

$IC_{50}$ Results for DN57 and RI57 on DENV Clades 1-4.

| Peptide | Virus | $IC_{50}$ ([μM]) | ±sd |
|---|---|---|---|
| DN57 | DENV1 | 8.3 | 2.1 |
| | DENV2 | 6.1 | 3.1 |
| | DENV3 | 12.9 | 5.6 |
| | DENV4 | 8.6 | 3 |
| RI57 | DENV1 | 4.6 | 3.2 |
| | DENV2 | 7.4 | 2.8 |
| | DENV3 | 5.9 | 4.8 |

Assays Mechanistically to Characterize DN57 and RI57
DN57 or RI57 Versus DENV2, Pre-binding FFU Assay Experiments were conducted further to characterize observed inhibitory effects and determine whether these may have been due to unintended interference owing to modifications of target LLC-MK2 cell surfaces. RI57 was incubated with target cells for 1 h at 4° C., the monolayer cells were then rinsed with PBS, and approximately 200 FFU of DENV2 allowed to infect the cells at 4° C. Agarose overlays, incubation, and immunological detection tests were conducted as described above for the focus-forming assay.

Pre-Binding Focus-Forming Assay with DN57 and RI57 Against DENV2

In this assay, DN57 or RI57 was added to target cells for 1 h prior to infection with DENV2 to determine whether these peptides inhibit entry through interaction directly with target cells. Treatment of target cells with the peptides prior to DENV2 infection produced no evidence of inhibition, indicating they do not function by interacting with, or modifying, the target cell surface and, furthermore, these peptides must be present concurrently with the virus to inhibit entry. Table 5. (and also FIG. 7) presents results showing that peptide binding can be reversible. Incubation with 10 µM/1 h at 20° C. of either peptide inhibits infection as shown in Table 2. (and FIG. 5.). Introducing a step diluting the concentration of peptide 10-fold after incubating/1 h at 20° C. and then infecting immediately thereafter reverses this inhibition. Errors around the means are depicted as ±sd.

TABLE 5

Pre-binding FFU Assay Shows Peptide Binding is Reversible (for DN57 or RI57 Versus DENV2).

| Treatment Condition | % DENV2 Infection Inhibition | ±sd |
| --- | --- | --- |
| DN57 | 83.1 | 8.6 |
| DN57, PBS Rinse | −2.8 | 9.9 |
| RI57 | 60.6 | 5.6 |
| RI57, PBS Rinse | −15.7 | 12.0 |

DN57 Versus DENV2, Post-Binding FFU Assay

Experiments were conducted further to characterize observed inhibitory effects as to whether these may have been due to interference with interactions occurring pre-binding, versus post-binding, of virions and LLC-MK2 target cells. An estimated 200 FFU of DENV2 were allowed to interact with target cells for 1 h at 4° C., permitting binding while preventing internalization. Unbound virus was washed off with PBS at 4° C., DN57 added, and the cultures incubated at 4° C. for 1 h, again washed in 4° C. PBS, and then warmed to 37° C. Finally, agarose overlays, incubation, and immunological detection assays were performed as described for the focus-forming assay.

Inasmuch as it was determined that inhibition by DN57 occurs at a viral-entry step, whether infection could still be inhibited after virus had bound to the surface of target cells was tested. In these experiments, virus was allowed to bind to cells at 4° C., then treated with increasing concentrations of DN57 before warming the cells to 37° C. providing conditions in favor of viral progression. Treatment of cells with DN57 following virus binding to cells, but before entry, inhibits DENV-2 infection (data not shown here, see Costin, et al., 2010).

DN57 Versus DENV2, Post-Entry FFU Assay

Experiments were conducted further to characterize observed inhibitory effects to determine whether they actually may have been due to interference with post-entry steps in the viral life cycle. To this end, approximately 200 FFU of DENV2 (without DN57) were allowed the opportunity to bind and then enter target LLC-MK2 cells for 1 h at 37° C. as described for the focus-forming assay. Any unbound virus was then removed by rinsing with PBS. Next, DN57 was added to the cells post-entry for 1 h at 37° C. Cultures again were washed with PBS and agarose overlays, incubation, and immunological detection assessments were performed as described for the focus-forming assay.

When DENV-2 was allowed to infect LLC-MK2 cells before peptide was added to the cells, no inhibition of viral replication was observed at any DN57 concentration in the assays (data not shown here, see Costin, et al., 2010), indicating that the peptide is not active during a post-infection step.

Quantitative Real-time Reverse Transcription PCR (qRT-PCR) Virus-Binding Assay

Further to characterize DENV binding to host cells, experiments were conducted to analyze the first step in the process of infection. Infection of LLC-MK2 target cells in six-well plates was executed in duplicate using $10^5$ FFU of DENV2 pre-incubated 45 min at 4° C. with either DN57, or RI57 peptide, or pooled heterotypic anti-DENV human serum. Following said 45 min exposure at 4° C., infected monolayers were washed with PBS and harvested by cell scraping, added to a 1.5 ml microfuge tube containing 350 µl AR-200 silicone oil (Sigma-Aldrich, St. Louis, Mo.), mixed with 150 µl silicone fluid (Thomas, Swedesboro, N.J.), and microfuge spun 1 min at 14,000 rpm to separate unbound virus from cell-bound virus. The tubes were then submerged in liquid nitrogen for 30 sec to freeze the contents. The cell pellets with (or without) bound virus were recovered by removing the bottoms of the tubes with small wire clippers and placing them in 15 ml conical tubes. By means of the Qiagen Viral RNA Extraction Kit (Qiagen, Chatsworth, Calif.), viral RNA was extracted from cell pellets.

Using the Quantitect SYBR Green RT-PCR kit (Qiagen Inc., Chatsworth, Calif.), qRT-PCR was performed on the extracted RNA. Manufacturer's specifications and amplification protocols were followed utilizing dengue-specific primers: (DenF: 5-TTAGAGGAGACCCCTCCC-3 and DenR: 5-TCTCCTCTAACCTCTAGTCC-3). Accordingly, reactions were performed in ~20 µl total volume (10 µl 2×SYBR green master mix, 0.5 µ/L 10 µM of each primer, 0.2 µl reverse transcriptase, and 5 µl viral RNA) by means of a Lightcycler thermal cycler (Roche Diagnostics, Carlsbad, Calif.). The following amplification protocol was used: 50° C. for 20 min to reverse transcribe the RNA; 95° C. for 15 min to activate the HotStart Taq DNA Polymerase; 45 PCR cycles: 94° C. for 15 sec; 50° C. for 15 sec; 72° C. for 30 sec; and fluorescence data acquisition was the final step. Melting curve analysis was then performed using a slow increase in temperature (0.1° C./sec) up to 95° C. The threshold cycle, representing the number of cycles at which the fluorescence of the amplified product was significantly above background, was calculated using the Roche Lightcycler 5.3.2 software.

qRT-PCR Virus-Binding Assay with DN57 and RI57 Against DENV2

Figure 9:
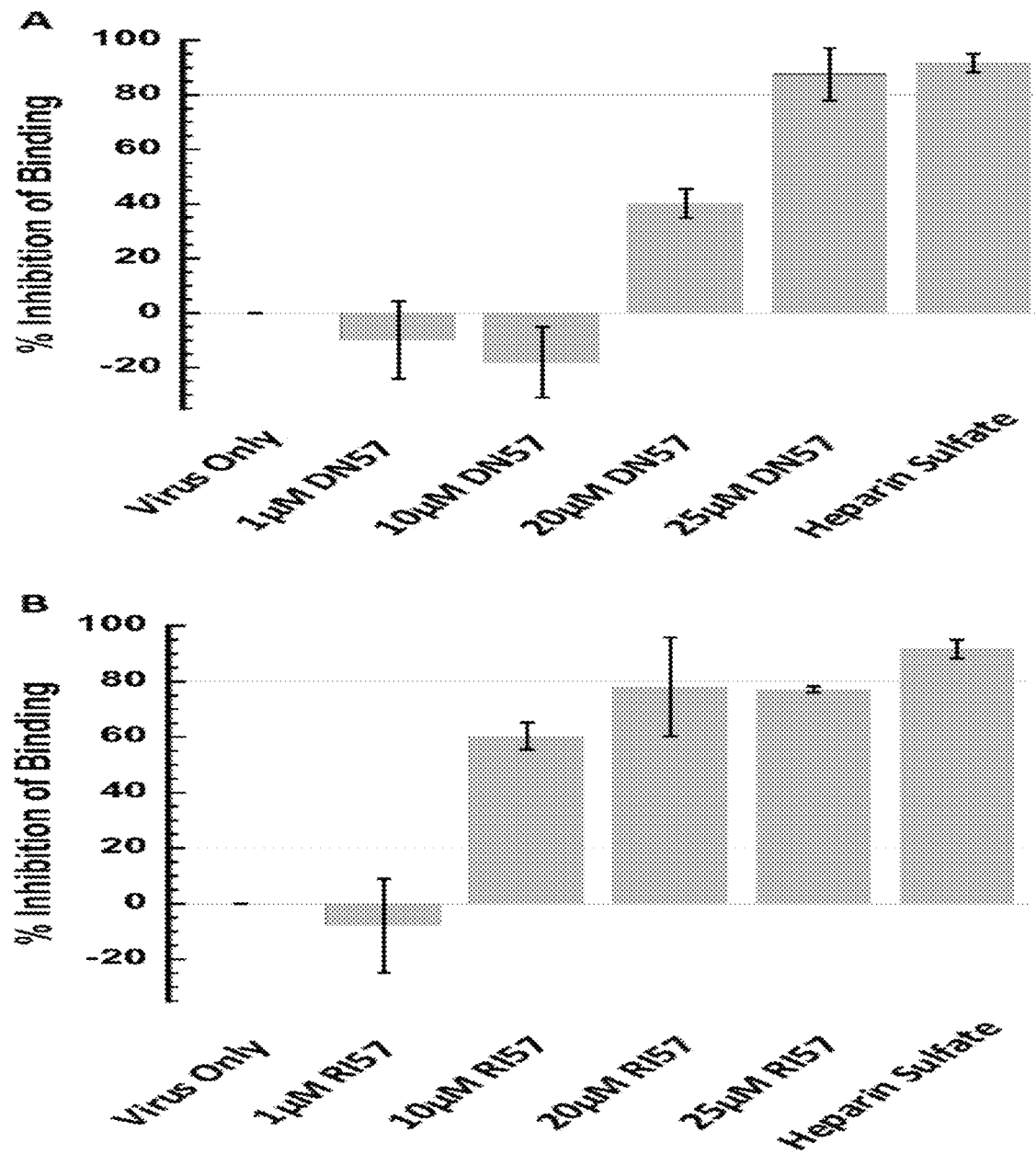
FIG. 9 graphs DN57 and RI57 binding inhibition of dengue virus to target host cells (see table 6.).

To test whether DN57 and RI57 interfere directly with virus binding to target cells, binding assays were conducted using qRT-PCR to monitor attachment of virus to target cells. In these experiments, virus was co-incubated with DN57 or RI57 for 45 min at 4° C. and then allowed to infect target cells at 4° C. for 45 min. The cells were scraped off the plates and centrifuged through an oil mixture with a density that allowed passage of the cells, but not free virus, to the bottom of the tube. RNA was then extracted from the cell pellets and amplified with DENV2-specific primers to quantitate the presence of virus. Table 6. (and also FIG. 9) depicts the results showing that both (A) DN57 and (B) RI57 inhibit binding of virus to cells. As previously observed, heparin sulfate dramatically reduces binding of dengue virus to cells and proves a useful control. Error bars represent ±sd of the means.

TABLE 6 qRT-PCR Virus-binding Assay Shows Both DN57 and RI57 Inhibit Binding of DENV2 to Cells.

| Exposure Condition | % Infection Inhibition | ±sd |
|---|---|---|
| DENV2 + nil | 0.0 | 0.0 |
| DENV2 + Trypsin + STI | −0.4 | 6.0 |
| DENV2 + 20 uM DN57 | 96.4 | 3.1 |
| DENV2 + 20 uM DN57 + Trypsin + STI | 5.2 | 11.5 |
| DENV2 + 10 uM RI57 | 98.6 | 18.7 |
| DENV2 + 10 uM RI57 + Trypsin + STI | 99.0 | 19.4 |

RI57 Resists Trypsin Digestion

Figure 10:
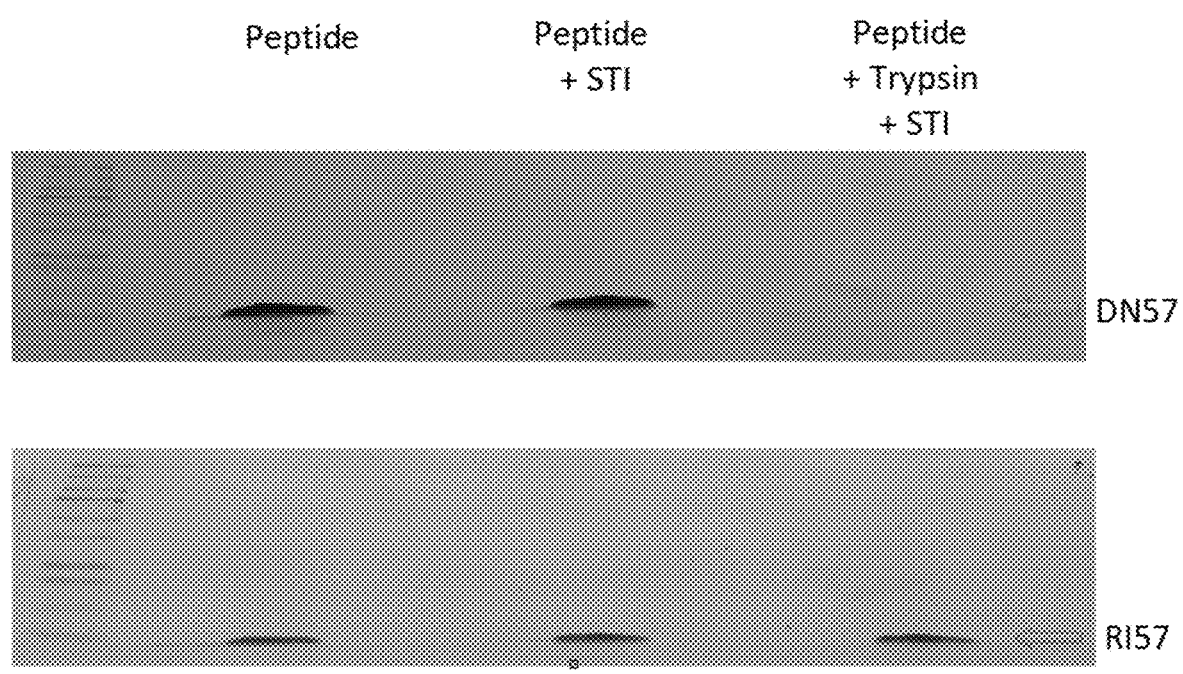
FIG. 10 indicates the resistance of RI57 to trypsin cleavage.

RI57 is resistant to trypsin cleavage and DN57 is not, as indicated in FIG. 10. The image documents 10-20% gradient gels run electrophoretically (e-gel), labeled with Imperial Protein Stain, and photographed. An e-gel was performed for each peptide, stained with Imperial stain, and photographed. The arrow markers show both the identity of the peptide run and its final location after migration. For each peptide assessment, lanes 1 contain peptide alone; lanes 2, peptide plus soybean trypsin inhibitor (STI); and lanes 3, peptide incubated in trypsin at 37° C. before adding STI. Clearly, DN57 was degraded, RN57 remained intact.

RI57 is Resistant to Degradation in Normal Human Serum (NETS)

Figure 11:
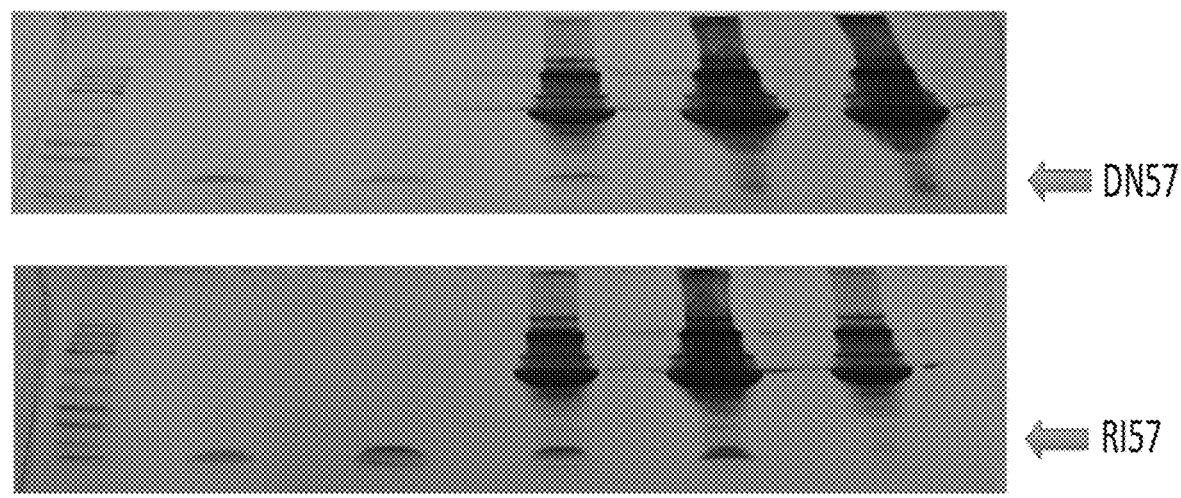
FIG. 11 indicates RI57 resistance to degradation in human serum.

NHS contains numerous proteolytic enzymes including plasmin, thrombin, Hageman factor; leukocyte enzymes including elastase, cathepsin G; and many others potentially capable of degrading candidate therapeutic peptides. As FIG. 11 shows, 10-20% gradient e-gels were run, stained with Imperial Protein Stain, and photographed. Again, the arrow bars indicate the identity of each tested peptide and where it finally migrated in the e-gel assay. Lane 1 contains peptide alone/time=0; lane 2, peptide at 37° C./time=24 h; lane 3, peptide in a 1:2 dilution of NHS/time=0; lane 4, peptide in a 1:2 dilution of NHS @ 37° C./time=24 h; and lane 5, a 1:2 dilution of NHS with no peptide at 37° C./time=24 h. N.b., lanes 4 show DN57 is absent and RI57 remains completely intact.

Trypsin Exposure Does Not Affect RI57's DENV2 Inhibitory Activity

Figure 12:
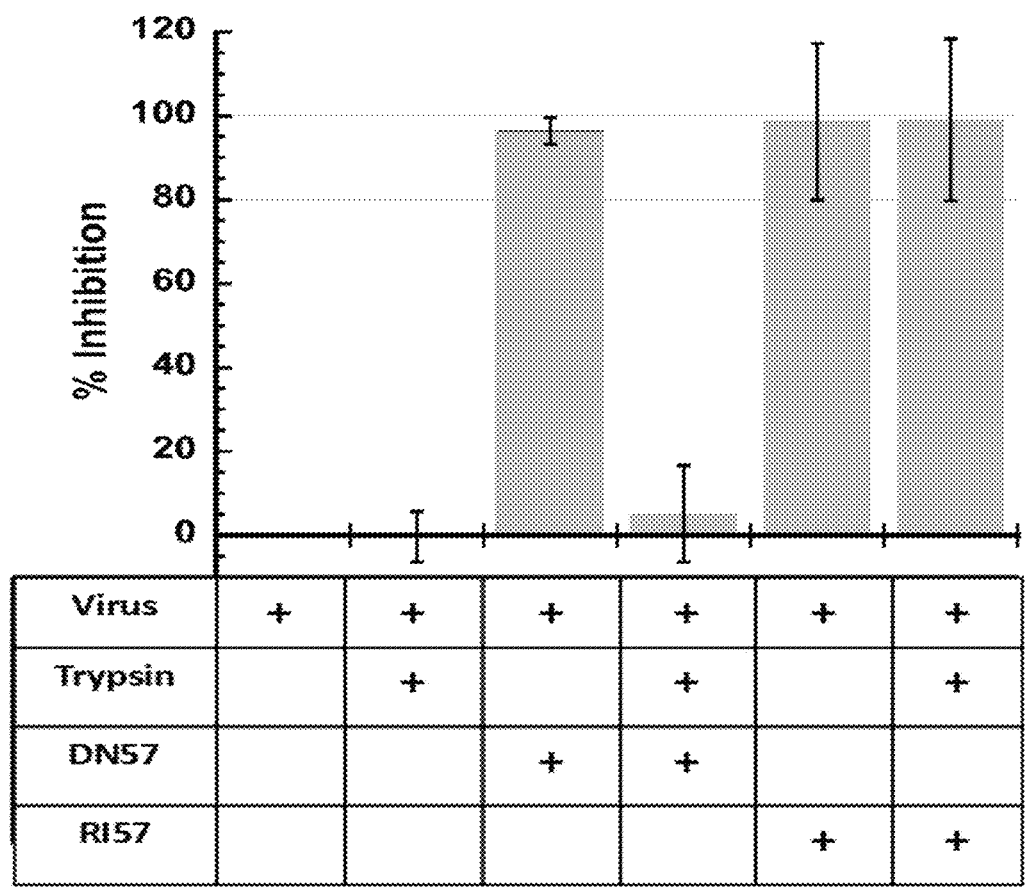
FIG. 12 charts DN57 as sensitive to trypsin, whereas RI57 is trypsin resistant (see table 7.).

Table 7. (and also FIG. 12) shows results of trypsin exposure on peptides RI57 and DN57 in terms of DENV2 infectivity as measured by the LLC-MK2 FFU assay. The peptides were exposed to trypsin for ten minutes at 37° C. before STI was added and further incubated ten minutes. The resulting peptide, in each case, was incubated with DENV2 for 1 hour at 20° C. and then this preparation used to infect confluent LLC-MK2 monolayers. Distinctively, RI57 retained its inhibitory activity, whereas DN57 did not. Thus, trypsin exposure does not affect RI57's DENV2 inhibitory activity.

TABLE 7

Trypsin Exposure Does Not Affect RI57's DENV2 Inhibitory Activity.

| Exposure Condition | % Infection Inhibition | ±sd |
|---|---|---|
| DENV2 + nil | 0.0 | 0.0 |
| DENV2 + Trypsin + STI | −0.4 | 6.0 |
| DENV2 + 20 uM DN57 | 96.4 | 3.1 |
| DENV2 + 20 uM DN57 + Trypsin + STI | 5.2 | 11.5 |
| DENV2 + 10 uM RI57 | 98.6 | 18.7 |
| DENV2 + 10 uM RI57 + Trypsin + STI | 99.0 | 19.4 |

Based upon the foregoing disclosure, it should now be evident that the use of virus-to-cell fusion and entry-inhibitory peptides bindable to regions of the dengue virus E protein, as potential candidates for the development of anti-viral compounds and as described herein, will carry out the objectives set forth hereinabove. Further, experimental evidence supports the conclusion that R157 is severally an effective inhibitor of DENV and Zika virus fusion, entry, and infection of target host cells and also is resistant to digestion by naturally-occurring proteolytic agents. Therefore, and finally, it is to be understood that any apparent and reasonable variations fall within the scope of the claimed invention and thus, the selection of specific component elements can be determined without departing from the spirit of the invention herein disclosed and described.

We claim:

1. A protease-resistant flavivirus-targeted cell entry-inhibitory peptide consisting of 28 amino acids arranged in an enantiopure, D-amino acid sequence presented as SEQ ID NO: 1.

2. The cell entry-inhibitory peptide of claim 1, wherein the cell entry-inhibitory peptide blocks a flaviviral class II envelope protein.

3. The cell entry-inhibitory peptide of claim 2, wherein the class II envelope protein is a flaviviral E protein.

4. A pharmaceutical composition comprising the cell entry-inhibitory peptide of claim 1 and a biocompatible carrier.

5. The pharmaceutical composition of claim 4, wherein the biocompatible carrier is selected from the group consisting of saline, buffered saline, dextrose, surfactant/spreading agent, and water.

* * * * *

SEQUENCE LISTING

```
<160> NUMBER OF SEQ ID NOS: 1

<210> SEQ ID NO 1
<211> LENGTH: 28
<212> TYPE: PRT
<213> ORGANISM: artificial sequence
<220> FEATURE:
<223> OTHER INFORMATION: laboratory-synthesized enantiopure D-peptide

<400> SEQUENCE: 1

Pro Trp Gln Gln Asn Gln Lys Asn Lys Gly Pro Asn Tyr Pro Leu Arg
1               5                   10                  15

Leu Arg His Phe Trp His Arg Trp Val Met Trp Arg
            20                  25
```